(12) United States Patent
Shaklee et al.

(10) Patent No.: US 8,748,595 B2
(45) Date of Patent: Jun. 10, 2014

(54) METHODS FOR FUCOIDAN PURIFICATION FROM SEA WEED EXTRACTS

(75) Inventors: Patrick N. Shaklee, Arlington, WI (US); Jennifer Bahr-Davidson, Redwood City, CA (US); Srinivasa Prasad, Palo Alto, CA (US); Kirk Johnson, Moraga, CA (US)

(73) Assignees: Baxter International Inc., Deerfield, IL (US); Baxter Healthcare S.A., Glattpark (CH)

( * ) Notice: Subject to any disclaimer, the term of this patent is extended or adjusted under 35 U.S.C. 154(b) by 1059 days.

(21) Appl. No.: 12/449,712

(22) PCT Filed: Feb. 1, 2008

(86) PCT No.: PCT/US2008/001425
§ 371 (c)(1),
(2), (4) Date: Feb. 25, 2010

(87) PCT Pub. No.: WO2008/103234
PCT Pub. Date: Aug. 28, 2008

(65) Prior Publication Data
US 2010/0144667 A1    Jun. 10, 2010

Related U.S. Application Data

(60) Provisional application No. 60/891,287, filed on Feb. 23, 2007.

(51) Int. Cl.
*C07H 15/04* (2006.01)
*A61K 31/715* (2006.01)

(52) U.S. Cl.
USPC ......... 536/127; 536/122; 536/123.1; 536/124

(58) Field of Classification Search
CPC ... C08B 37/0075; C07H 15/04; A61K 31/715
USPC ............ 536/122, 123.1, 124; 514/54, 56, 834
See application file for complete search history.

(56) References Cited

U.S. PATENT DOCUMENTS

| | | | | |
|---|---|---|---|---|
| 4,431,546 | A * | 2/1984 | Hughes et al. | ................. 210/656 |
| 6,593,311 | B2 | 7/2003 | Sakai et al. | |
| 2005/0282771 | A1 | 12/2005 | Johnson | |
| 2006/0088912 | A1 * | 4/2006 | Yan et al. | ..................... 435/69.1 |

FOREIGN PATENT DOCUMENTS

| | | | |
|---|---|---|---|
| EP | 1327448 A1 * | 7/2003 | |
| JP | 07215990 A | 8/1995 | |
| JP | 2002-262788 A | 9/2002 | |
| JP | 3371124 B2 * | 1/2003 | |
| KR | 10-0555844 | 12/2006 | |

OTHER PUBLICATIONS

Liu et al ("Improved coagulation in bleeding disorders by non-anticoagulant sulfated polysaccharides (NASP)", Thrombosis and Haemostasis (2006), 95(1), pp. 68-76).*
Nagaoka et al ("Structural study of fucoidan from *Cladosiphon okamuranus* Tokida", Glycoconjugate Journal 16, 19-26, 1999).*
Kitamura et al ("Fucoidan from brown seaweed *Laminaria augustata* var. lingissima", Agricultural and Biological Chemistry, Japan SOC. for Bioscience, Biotechnology and Agrochem, vol. 55, No. 2 Jan. 1991) in view of Owa (JP41032508 A).*
Suzuki et al ("Adsorption and removal of oxo-anions of arsenic and selenium on the zirconium(IV) loaded polymer resin functionalized with diethylenetriamine-N,N,N',N'-polyacetic acid",J. Environmental Monitoring: Dec. 2002;2(6):550-5).*
Gao et al ("Development of column-pretreatment chelating resins for matrix elimination/multi-element determination by inductively coupled plasma-mass spectrometry", Analyst, Dec. 2002;127(12):1713-9).*
Mabeau S et al, "Fractionation and Analysis of Fucans From Brown Algae", Phytochemistry (Oxford), vol. 29. No. 8, pp. 2441-2446, (1990).
Marais M-F et al, "A fucoidan fraction from *Ascophyllum nodosum*", Carbohydrate Research, Elsevier Scientific Publishing Company, vol. 336, No. 2, pp. 155-159, (2001).
Nishino T et al, "Isolation and Partial Characterization of a Novel Amino Sugar-Containing Fucan Sulfate From Commercial *Fucus vesiculosus* Fucoidan", Carbohydrate Research. Elsevier Scientific Publishing Company, vol. 255, pp. 213-224, (1994).
Springer G F et al, "Isolation of anticoagulant fractions from crude fucoidin", Proceedings of the Society for Experimental Biology & Medicine, Academic Press Inc., vol. 94, No. 2, pp. 404-409, (1957).
Notice of Office Action mailed on Mar. 24, 2014, Korean patent application No. 7019831/2009, 6 pages.

* cited by examiner

*Primary Examiner* — Patrick Lewis
*Assistant Examiner* — Everett White
(74) *Attorney, Agent, or Firm* — Khin K. Chin; Bret E. Field; Bozicevic, Field & Francis, LLP (57) ABSTRACT

Methods for purifying fucoidan in extracts from brown seaweed are disclosed. In particular, methods of purifying fucoidan in the extract to remove heavy metal ions, bacterial and endotoxin contaminants, and other impurities are disclosed. The methods include the use of a chelating agent, selective precipitation, and filtration.

25 Claims, 3 Drawing Sheets

Unprocessed (050316)

Processed Lot #1

Processed Lot #2

US 8,748,595 B2

METHODS FOR FUCOIDAN PURIFICATION FROM SEA WEED EXTRACTS

This application is a §371 filing from PCT/US2008/001425, filed Feb. 1, 2008, and claims the benefit under 35 U.S.C. §119(e)(1) of U.S. Provisional Application No. 60/891,287, filed Feb. 23, 2007, which applications are incorporated herein by reference in their entireties and from which applications priority is claimed pursuant to the provisions of 35 U.S.C. §§119/120.

TECHNICAL FIELD

The present invention relates generally to the production of fucoidan (also termed AV513 herein). More particularly, the invention relates to methods of purifying fucoidan extract to remove heavy metal ions, bacterial and endotoxin contaminants, and other impurities without affecting the desired biological activity.

BACKGROUND

Normal blood coagulation is a complex physiological and biochemical process that is regulated at several levels. The process of blood coagulation involves activation of a coagulation factor cascade leading to fibrin formation and platelet aggregation along with local vasoconstriction (reviewed by Davie et al., *Biochemistry* 30:10363, 1991). The clotting cascade is composed of an "extrinsic" pathway thought to be the primary means of normal coagulation initiation and an "intrinsic" pathway contributing to an expanded coagulation response. The normal response to a bleeding insult involves activation of the extrinsic pathway. Activation of the extrinsic pathway is initiated when blood comes in contact with tissue factor (TF), a cofactor for factor VII that becomes exposed or expressed on tissues following insult. TF forms a complex with FVII that facilitates the production of FVIIa. FVIIa then associates with TF to convert FX to the serine protease FXa, which is a critical component of the prothrombinase complex. The conversion of prothrombin to thrombin by the FXa/FVa/calcium/phospholipid complex stimulates the formation of fibrin and activation of platelets, all of which is essential to normal blood clotting. Normal hemostasis is further enhanced by intrinsic pathway factors IXa and VIIIa, which also convert FX to FXa. See also Weitz, J. I., et al., *Chest,* 126 (3), September 2004 (Suppl), 265S.

Sulfated polysaccharides are a class of molecules characterized by a plethora of biological activities with often favorable tolerability profiles in animals and humans. These polyanionic molecules are often derived from plant and animal tissues and encompass a broad range of subclasses including heparins, glycosaminoglycans, fucoidans, carrageenans, pentosan polysulfates, and dermatan or dextran sulfates. Heparin-like sulfated polysaccharides exhibit differential anticoagulant activity mediated through antithrombin III and/or heparin cofactor II interactions (Toida T C, Linhardt, R J., *Trends in Glycoscience and Glycotechnology* 2003;15:29-46).

While one such sulfated polysaccharide, oral heparin, has been considered for development as an anticoagulant (A Dunn, *Idrugs,* 3:817-824, 2000), heparin is inadequate because of its serious complications which include intraoperative and postoperative bleeding, osteoporosis, alopecia, heparin resistance, heparin rebound, heparin-induced thrombocytopenia (HIT), heparin-induced thrombocytopenia thrombosis syndrome (HITTS), and other disadvantages including multiple days for anticoagulation to attenuate after discontinuing the drug (Iqbal O, et al., Fareed J, *Expert Opin Emerg Drugs* 6:111-135, 2001; Roberts, H R, *Anesthesiology* 100:722-730, 2004). Heparin is conventionally administered parenterally, and possesses an oral uptake level of only about 1% (Fitton, J. H., *Glycoscience*, The Nutrition Science Site, modified Jan. 1, 2005).

In contrast to heparin, another sulfated polysaccharide, fucoidan, a sulfated polysaccharide isolated from sea algae, has been shown to regulate (i.e., promote) coagulation (U.S. Patent Publication No. 2005/0282771). Specifically, fucoidans, when administered at low concentrations in vitro, or low subcutaneous doses in vivo, provide improved (accelerated) clotting in hemophilic settings through extrinsic pathway activation (Liu, T., et al., and Johnson, K. W., Thrombosis and Haemostasis, 95:68-76, 2006), demonstrating a procoagulant activity. At higher doses fucoidan can have an anti-coagulant effect similar to heparin. In light of the problems associated with current anticoagulants like heparin or warfarin, there clearly remains a need for agents, such as fucoidan, that can overcome one or more of the problems associated with currently available anticoagulant therapy.

Thus, there remains a need for an improved method to cost-effectively and efficiently produce fucoidan enriched extract with optimal activity for procoagulant or anticoagulant therapeutic use.

SUMMARY OF THE INVENTION

The present invention is based on the discovery of a method for purifying fucoidan from seaweed extract. The method provides for high yields of fucoidan substantially free of heavy metal ions, bacterial and endotoxin contaminants, and other impurities.

Accordingly, the subject invention includes a method for enriching fucoidan from a heterogeneous mixture, the method comprising:
  (a) providing a source of fucoidan;
  (b) removing heavy metal ions from said source by treating with a chelating agent to produce a first fucoidan mixture;
  (c) selectively precipitating fucoidan present in said first fucoidan mixture to remove contaminants;
  (d) resuspending fucoidan-containing precipitate in aqueous solution to produce a second fucoidan mixture;
  (e) repeating steps (c) and (d) one or more times; and
  (f) filtering the aqueous solution comprising fucoidan to remove bacterial and endotoxin contaminants to yield purified fucoidan extract. In one embodiment, the fucoidan possesses from 5 to 25 percent by weight sulfur. In another embodiment, the fucoidan is of algal origin. In a preferred embodiment, the fucoidan is derived from the genus *Fucus* or *Laminaria*. Exemplary fucoidans are those derived from *Fucus vesiculosis* or from *Laminaria japonica* or other sources including, but not limited to *Undaria pinnitifada* and *Ascophyllum nodosum*.

In certain embodiments, the chelating agent is selected from the group consisting of ethylene diamine tetra acetic acid (EDTA), ethyleneglycol-bis-(beta-aminoethyl ether)N,N,N',N'-tetraacetic acid (EGTA), 2,3-dimercaptopropanel-1-sulfonic acid (DMPS), and 2,3-dimercaptosuccinic acid (DMSA). In a preferred embodiment, the chelating agent is EDTA. In certain embodiments, the chelating agent is immobilized on a solid support. In one embodiment, the chelating agent is an iminodiacetate chelating resin.

In certain embodiments, the fucoidan is selectively precipitated one or more times with ethanol, wherein the concentration of ethanol in the fucoidan mixture is about 40% to 50% (v/v). In certain embodiments, the pH is maintained between about pH 5.7 to about pH 6.0. In a preferred embodiment, the pH is adjusted to about pH 5.95. In certain embodiments, NaCl is added to the fucoidan mixture at a concentration of about 20-24 g/liter.

In another aspect, the invention provides a composition comprising fucoidan produced by any of the methods described herein. In one embodiment, the fucoidan possesses from 5 to 25 percent by weight sulfur. In another embodiment, the fucoidan is of algal origin. In a preferred embodiment, the fucoidan is derived from the genus *Fucus* or *Laminaria*. Exemplary fucoidans are those derived from *Fucus vesiculosis* or from *Laminaria japonica* or from *Chorda filum, Cladosiphon okamuranus, Undaria pinnatifida, Leathesia difformis, Ascophyllum nodosum, Ecklonia kurome, Pelvetia fastigiata, Saundersella simplex, Chordaria flagelliformis*, or any other species of sea plant or animal containing fucoidan. In a preferred embodiment, the fucoidan is biologically active, for example, having pro-coagulant activity. In certain embodiments, the composition may further comprise a pharmaceutically acceptable excipient.

In another aspect, the invention provides a method for treating a subject in need of enhanced blood coagulation comprising administering a therapeutically effective amount of a composition comprising fucoidan, produced by any of the methods described herein, to said subject. In certain embodiments, the subject has a bleeding disorder selected from the group consisting of a chronic or acute bleeding disorder, a congenital coagulation disorder caused by a blood factor deficiency, and an acquired coagulation disorder. In other embodiments, the cause of the need for enhanced blood coagulation is prior administration of an anticoagulant, surgery, or other invasive procedure. In certain embodiments, the fucoidan is administered at a dosage of about 0.01 mg/kg to about 100 mg/kg.

These and other embodiments of the subject invention will readily occur to those of skill in the art in view of the disclosure herein.

DETAILED DESCRIPTION OF THE INVENTION

The practice of the present invention will employ, unless otherwise indicated, conventional methods of protein chemistry, biochemistry, molecular biology, and pharmacology, within the skill of the art. Such techniques are explained fully in the literature. See, e.g., *Protein Purification Methods: A Practical Approach*, (E. L. V. Harris and S. Angal, Eds., 1989); *Protein Purification Applications: A Practical Approach*, (E. L. V. Harris and S. Angal, Eds., 1990); T. E. Creighton, *Proteins: Structures and Molecular Properties* (W.H. Freeman and Company, 1993); A. L. Lehninger, *Biochemistry* (Worth Publishers, Inc., current addition); *Methods In Enzymology* (S. Colowick and N. Kaplan eds., Academic Press, Inc.); Morrison and Boyd, *Organic Chemistry* (Allyn and Bacon, Inc., current addition); J. March, *Advanced Organic Chemistry* (McGraw Hill, current addition); *Remington: The Science and Practice of Pharmacy*, A. Gennaro, Ed., 20th Ed.; and *Goodman & Gilman The Pharmacological Basis of Therapeutics*, J. Griffith Hardman, L. L. Limbird, A. Gilman, 10th Ed.

All publications, patents and patent applications cited herein, whether supra or infra, are hereby incorporated by reference in their entireties.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

1. Definitions

In describing the present invention, the following terms will be employed, and are intended to be defined as indicated below.

It must be noted that, as used in this specification and the appended claims, the singular forms "a", "an" and "the" include plural references unless the content clearly dictates otherwise. Thus, for example, reference to "fucoidan" includes a mixture of two or more such fucoidans, and the like.

As used herein, the term "about" means ± about 10% of the value it modifies.

The term "biologically active" refers to a protein having structural, regulatory, or biochemical functions of a naturally occurring molecule.

The term "fucoidan," as used herein, refers to a sulfated alpha-L-fucan found in many sea plants and animals. Fucoidan is particularly abundant in the cell walls of brown algae and includes fucoidans derived from the genus *Fucus* (e.g., *Fucus vesiculosis, Fucus evanescens, Fucus distichus*, and *Fucus serratus*) or *Laminaria* (e.g., *Laminaria japonica, Laminaria religiosa*, and *Laminaria abyssalis*). Fucoidan also includes fucoidans derived from *Chorda filum, Cladosiphon okamuranus, Undaria pinnatifida, Leathesia difformis, Ascophyllum nodosum, Ecklonia kurome, Pelvetia fastigiata, Saundersella simplex, Chordaria flagelliformis*, or any other species of sea plant or animal containing fucoidan. In addition, the term fucoidan includes biologically active fragments, derivatives, or analogues thereof. Fucoidan may include fragments of fucoidan generated by degradation (e.g., hydrolysis) of larger fucoidan molecules. Degradation can be achieved by any of a variety of means known to those skilled in the art including treatment of fucoidan with acid, base, heat, or enzymes to yield degraded fucoidan. Fucoidans may also be chemically altered and may have modifications, including but not limited to, sulfation, polysulfation, acetylation, esterification, and methylation.

"Substantially purified" generally refers to isolation of a substance (e.g., fucoidan) such that the substance comprises the majority percent of the sample in which it resides. Typically in a sample, a substantially purified component comprises 50%, preferably 80%-85%, more preferably 90-95% of the sample.

A composition containing A is "substantially free of" B when at least about 80% by weight of the total A+B in the composition is A. Preferably, A comprises at least about 85% to 95% by weight of the total of A+B in the composition.

An "anticoagulant" as used herein refers to any agent capable of preventing or slowing clot formation.

A "procoagulant" as used herein refers to any agent capable accelerating clot formation.

A "chelating agent" as used herein refers to a chemical compound, peptide or protein capable of binding a metal. Examples of chelating agents include ethylene diamine tetra acetic acid (EDTA), ethyleneglycol-bis-(beta-aminoethyl ether)N,N,N',N'-tetraacetic acid (EGTA), 2,3-dimercaptopropanel-1-sulfonic acid (DMPS), and 2,3-dimercaptosuccinic acid (DMSA), and the like. The chelating agent may be immobilized on a solid support (e.g., iminodiacetate chelating resin).

The term "derived from" is used herein to identify the original source of a molecule but is not meant to limit the method by which the molecule is made which can be, for example, by chemical synthesis or recombinant means.

By "derivative" is intended any suitable modification of the reference molecule of interest or of an analog thereof, such as sulfation, acetylation, glycosylation, phosphorylation, polymer conjugation (such as with polyethylene glycol), or other addition of foreign moieties, so long as the desired biological activity (e.g., clotting activity) of the reference molecule is retained. Fucoidan may be chemically altered, for example, to improve procoagulant function. Such modifications may include, but are not limited to, sulfation, polysulfation, esterification, and methylation. Methods for making analogs and derivatives are generally available in the art.

By "fragment" is intended a molecule consisting of only a part of the intact full-length sequence and structure. A fragment of a fucoidan may be generated by degradation (e.g., hydrolysis) of a larger fucoidan polysaccharide. Active fragments of fucoidan will generally include at least about 2-20 saccharide units of the full-length polysaccharide, preferably at least about 5-10 saccharide units of the full-length molecule, or any integer between 2 saccharide units and the full-length molecule, provided that the fragment in question retains biological activity, such as procoagulant activity.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, hydrobromide, and nitrate salts, or salts prepared with an organic acid, such as maleate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

"Active molecule" or "active agent" as described herein includes any agent, drug, compound, composition of matter or mixture which provides some pharmacologic, often beneficial, effect that can be demonstrated in-vivo or in vitro. This includes foods, food supplements, nutrients, nutriceuticals, drugs, vaccines, antibodies, vitamins, and other beneficial agents. As used herein, the terms further include any physiologically or pharmacologically active substance that produces a localized or systemic effect in a patient.

"Optional" or "optionally" means that the subsequently described circumstance may or may not occur, so that the description includes instances where the circumstance occurs and instances where it does not.

The terms "subject", "individual" or "patient" are used interchangeably herein and refer to a vertebrate, preferably a mammal. Mammals include, but are not limited to, murines, rodents, simians, humans, farm animals, sport animals and pets.

2. Modes of Carrying Out The Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

A. Production of Fucoidan

The present invention is based on the discovery of a purification procedure that allows for the isolation of fucoidan substantially free of heavy metal ions, bacterial and endotoxin contaminants, and other impurities. The method comprises a series of isolation steps, including treatment with a chelating agent to remove heavy metals, one or more selective precipitations to remove impurities, and filtration to remove bacterial and endotoxin contaminants.

In order to further an understanding of the invention, a more detailed discussion is provided below regarding methods of purifying fucoidan extracts.

Fucoidan

Any source of fucoidan extract can be used in the purification. Fucoidans are found in many sea plants and animals and are particularly abundant in the cell walls of brown algae (Phaeophyceae). For example, fucoidan derived from brown algae of the genus *Fucus* (e.g., *Fucus vesiculosis, Fucus evanescens, Fucus distichus*, and *Fucus serratus*) or *Laminaria* (e.g., *Laminaria japonica, Laminaria religiosa*, and *Laminaria abyssalis*) can be used in the purification. Alternatively, fucoidan from other sources, including but not limited to, *Chorda filum, Cladosiphon okamuranus, Undaria pinnatifida, Leathesia difformis, Ascophyllum nodosum, Ecklonia kurome, Pelvetia fastigiata, Saundersella simplex, Chordaria flagelliformis*, or any other species of sea plant or animal containing fucoidan can also be used in the practice of the invention.

Chelating Agents

Any chelating agent capable of binding metal ions can be used to remove metal ion contaminants from a heterogeneous mixture containing fucoidan. Examples of chelating agents include, but are not limited to, ethylene diamine tetra acetic acid (EDTA), ethyleneglycol-bis-(beta-aminoethyl ether)N, N,N',N'-tetraacetic acid (EGTA), 2,3-dimercaptopropanel-1-sulfonic acid (DMPS), and 2,3-dimercaptosuccinic acid (DMSA), and the like. Alternatively, a metal chelating resin comprising immobilized chelating groups can be used to remove metal ions from a sample containing fucoidan. For example, commercially available chelating resins containing the chelating ligand iminodiacetate (e.g., CHELEX 100 (Bio-Rad), DOWEX A1 (Dow Chemical Co.), and chelating resin (Hampton Research)) can be used. Chelating resin can be added to a fucoidan sample in batch and removed by centrifugation. Alternatively, metal ions can be removed from fucoidan samples by chromatography through a column containing chelating resin by methods well-known in the art.

Selective Precipitation of Fucoidan

The fucoidan extract is further purified by selective precipitation of fucoidan with ethanol. Selective precipitation removes some chelating agents and other contaminants from the fucoidan mixture. In certain embodiments, the fucoidan is selectively precipitated one or more times with ethanol at a concentration of about 40% to 50% (v/v) in the fucoidan mixture. Before the addition of ethanol to the fucoidan mixture, the pH of the fucoidan mixture is adjusted to between about pH 5.7 to about pH 6.0, and NaCl is added to the fucoidan mixture at a concentration of about 20-24 g/liter. After precipitation of the fucoidan, the supernatant is removed from the precipitated fucoidan, and the precipitated fucoidan is resuspended in aqueous solution. Repeated cycles of such purification can improve the purity of fucoidan.

Filtration

The fucoidan is filtered through a 0.2 μm positively charged filter to remove bacterial and endotoxin contaminants. The filtered product can be dried using lyophilization or spray drying. Typically, the yield of fucoidan will be about 50% or more, more preferably about 60% to about 80% or more.

Analysis of Purified Fucoidan

Fucoidan samples can be analyzed for purity and various properties, such as molecular weight, carbohydrate content, including fucose and xylose, heavy metal contamination, sulfate, and water. A number of analytical techniques can be used to characterize fucoidan samples, including but not limited to, high performance liquid chromatography (HPLC), elemental composition analysis, laser light scattering (LLS), inductively coupled plasma mass spectrometry (ICP-MS), and GC-MS.

B Pharmaceutical Compositions

The purified fucoidan can be formulated into pharmaceutical compositions optionally comprising one or more pharmaceutically acceptable excipients. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition of the invention can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the fucoidan or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the fucoidan (e.g., when contained in a drug delivery system) in the composition will vary depending on a number of factors, but will optimally be a therapeutically effective dose when the composition is in a unit dosage form or container (e.g., a vial). A therapeutically effective dose can be determined experimentally by repeated administration of increasing amounts of the composition in order to determine which amount produces a clinically desired endpoint.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000.

The compositions encompass all types of formulations and in particular those that are suited for injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. Examples of suitable diluents for reconstituting solid compositions prior to injection include bacteriostatic water for injection, dextrose 5% in water, phosphate buffered saline, Ringer's solution, saline, sterile water, deionized water, and combinations thereof. With respect to liquid pharmaceutical compositions, solutions and suspensions are envisioned. Additional preferred compositions include those for oral, ocular, or localized delivery.

The pharmaceutical preparations herein can also be housed in a syringe, an implantation device, or the like, depending upon the intended mode of delivery and use. Preferably, the fucoidan compositions described herein are in unit dosage form, meaning an amount of a conjugate or composition of the invention appropriate for a single dose, in a premeasured or pre-packaged form.

The fucoidan compositions herein may optionally include one or more additional agents, such as hemostatic agents, blood factors, or other medications used to treat a subject for a condition or disease. Particularly preferred are compounded preparations including one or more blood factors such as factor XI, factor XII, prekallikrein, high molecular weight kininogen (HMWK), factor V, factor VII, factor VIII, factor IX, factor X, factor XIII, factor II, factor VIIa, and von Willebrands factor. Fucoidan compositions may also include other procoagulants, such as an activator of the intrinsic coagulation pathway, including but not limited to, factor Xa, factor IXa, factor XIa, factor XIIa, and VIIIa, prekallekrein, and high-molecular weight kininogen; or and activator of the extrinsic coagulation pathway, including but not limited to, tissue factor, factor VIIa, factor Va, and factor Xa. Fucoidan compositions may include naturally occurring, synthetic, or recombinant clotting factors or fragments, variants or covalently modified derivatives thereof that retain biological activity (i.e., promote cloning). Alternatively, such agents can be contained in a separate composition from the fucoidan and co-administered concurrently, before, or after the fucoidan composition of the invention.

C. Administration

At least one therapeutically effective cycle of treatment with fucoidan wilt be administered to a subject. By "therapeutically effective cycle of treatment" is intended a cycle of treatment that when administered, brings about a positive therapeutic response with respect to treatment of an individual for a bleeding disorder. Of particular interest is a cycle of treatment with fucoidan that improves hemostasis. By "positive therapeutic response" is intended that the individual undergoing treatment according to the invention exhibits an improvement in one or more symptoms of a bleeding disorder, including such improvements as shortened blood clotting times and reduced bleeding and/or reduced need for factor replacement therapy.

Other therapeutically effective cycle of treatment with fucoidan will be administered as an anti-coagulant to subjects with pro-thrombotic conditions like deep vein thrombosis, arterial thrombosis and other cardiovascular and cancer diseases as a preventative and/or maintenance therapy.

In certain embodiments, multiple therapeutically effective doses of compositions comprising fucoidan and/or one or more other therapeutic agents, such as hemostatic agents, blood factors, or other medications will be administered. The compositions of the present invention are typically, although not necessarily, administered orally, via injection (subcutaneously, intravenously or intramuscularly), by infusion, or locally. The pharmaceutical preparation can be in the form of a liquid solution or suspension immediately prior to administration, but may also take another form such as a syrup, cream, ointment, tablet, capsule, powder, gel, matrix, suppository, or the like. Additional modes of administration are also contemplated, such as pulmonary, rectal, transdermal, transmucosal, intrathecal, pericardial, intra-arterial, intracerebral, intraocular, intraperitoneal, and so forth. The pharmaceutical compositions comprising fucoidan and other agents may be administered using the same or different routes of administration in accordance with any medically acceptable method known in the art.

In a particular embodiment, a composition of the invention is used for localized delivery of fucoidan, for example, for the treatment of bleeding as a result of a lesion, injury, or surgery. The preparations according to the invention are also suitable for local treatment. For example, fucoidan may be administered by injection at the site of bleeding or topically in the form of a solid, liquid, or ointment, preferably via an adhesive tape or a wound cover. Suppositories, capsules, in particular gastric-juice-resistant capsules, drops or sprays may also be used. The particular preparation and appropriate method of administration are chosen to target the site of bleeding.

In another embodiment, the pharmaceutical compositions comprising fucoidan and/or other agents are administered prophylactically, e.g. before planned surgery. Such prophylactic uses will be of particular value for subjects with known pre-existing blood coagulation disorders.

In another embodiment of the invention, the pharmaceutical compositions comprising fucoidan and/or other agents, are in a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition.

The invention also provides a method for administering a conjugate comprising fucoidan as provided herein to a patient suffering from a condition that is responsive to treatment with fucoidan contained in the conjugate or composition. The method comprises administering, via any of the herein described modes, a therapeutically effective amount of the conjugate or drug delivery system, preferably provided as part of a pharmaceutical composition. The method of administering may be used to treat any condition that is responsive to treatment with fucoidan. More specifically, the compositions herein are effective in treating bleeding disorders, including hemophilia A, hemophilia B, von Willebrand disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrands factor, a vitamin K deficiency, a disorder of fibrinogen, including afibrinogenemia, hypofibrinogenemia, and dysfibrinogenemia, an alpha$_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy.

Those of ordinary skill in the art will appreciate which conditions a specific fucoidan can effectively treat. The actual dose to be administered will vary depending upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case.

Generally, a therapeutically effective amount will range from about 0.01 mg/kg to 200 mg/kg of a fucoidan daily, more preferably from about 0.01 mg/kg to 20 mg/kg daily, even more preferably from about 0.02 mg/kg to 2 mg/kg daily. Preferably, such doses are in the range of 0.01-50 mg/kg four times a day (QID), 0.01-10 mg/kg QID, 0.01-2 mg/kg QID, 0.01-0.2 mg/kg QID, 0.01-50 mg/kg three times a day (TID), 0.01-10 mg/kg TID, 0.01-2 mg/kg TID, 0.01-0.2 mg/kg TID, 0.01-100 mg/kg twice daily (BID), 0.01-10 mg/kg BID, 0.01-2 mg/kg BID, or 0.01-0.2 mg/kg BID and 0.1 to 10% for topical single and multiple applications a day. The amount of compound administered will depend on the potency of the specific fucoidan and the magnitude or procoagulant effect desired and the route of administration.

A purified fucoidan extract (again, preferably provided as part of a pharmaceutical preparation) can be administered alone or in combination with other fucoidan extracts or therapeutic agents, such as hemostatic agents, blood factors, or other medications used to treat a particular condition or disease according to a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Preferred compositions are those requiring dosing no more than once a day.

Fucoidan can be administered prior to, concurrent with, or subsequent to other agents. If provided at the same time as other agents, the fucoidan can be provided in the same or in a different composition. Thus, fucoidan and other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising a fucoidan and a dose of a pharmaceutical composition comprising at least one other agent, such as a hemostatic agent or coagulation factor (e.g. FVIII or FIX), which in combination comprise a therapeutically effective dose, according to a particular dosing regimen. Similarly, fucoidan and one or more other therapeutic agents can be administered in at least one therapeutic dose. Administration of the separate pharmaceutical compositions can be performed simultaneously or at different times (i.e., sequentially, in either order, on the same day, or on different days), so long as the therapeutic effect of the combination of these substances is caused in the subject undergoing therapy.

F. Applications

Once purified, fucoidan extract can be used for a variety of purposes. In this regard, fucoidan can be used, e.g., as a procoagulant to promote blood clotting, reduce bleeding, counteract the effects of treatment of a subject with an anticoagulant, as a anti-inflammatory agent, as a anti-cancer agent, as a anti-viral agent or as a hematopoietic cell mobilizing agent The ability of purified fucoidan extract to promote clotting and reduce bleeding is readily determined using various in vitro clotting assays (e.g., dPT and aPTT assays) and in vivo bleeding models (e.g. tail snip or cuticle bleeding time determination in hemophilic mice or dogs). See, e.g., PDR Staff. Physicians' Desk Reference. 2004, Anderson et al. (1976) Thromb. Res. 9:575-580; Nordfang et al. (1991) Thromb Haemost. 66:464-467; Welsch et al. (1991) Thrombosis Research 64:213-222; Broze et al. (2001) Thromb Haemost 85:747-748; Scallan et al. (2003) Blood. 102:2031-2037; Pijnappels et al. (1986) Thromb. Haemost. 55:70-73; and Giles et al. (1982) Blood 60:727-730; herein incorporated by reference.

In one aspect, purified fucoidan extract may be used in the methods of the invention for improving hemostasis in treating bleeding disorders, particularly those associated with deficiencies of coagulation factors or for reversing the effects of anticoagulants in a subject. Fucoidan may be administered to a subject to treat bleeding disorders, including congenital coagulation disorders, acquired coagulation disorders, and hemorrhagic conditions induced by trauma. Examples of bleeding disorders that may be treated with Fucoidan include, but are not limited to, hemophilia A, hemophilia B, von Willebrand disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrands factor, a vitamin K deficiency, a disorder of fibrinogen, including afibrinogenemia, hypofibrinogenemia, and dysfibrinogenemia, an $alpha_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy. In certain embodiments, fucoidan is used to treat congenital coagulation disorders including hemophilia A, hemophilia B, and von Willebrands disease. In other embodiments, fucoidanis used to treat acquired coagulation disorders, including deficiencies of factor VIII, von Willebrand factor, factor IX, factor V, factor XI, factor XII and factor XIII, particularly disorders caused by inhibitors or autoimmunity against blood coagulation factors, or haemostatic disorders caused by a disease or condition that results in reduced synthesis of coagulation factors.

The needs of the patient will depend on the particular bleeding disorder being treated. For example, a fucoidan may be administered to treat a chronic condition (e.g., a congenital or acquired coagulation factor deficiency) in multiple doses over an extended period. Alternatively, a fucoidan may be administered to treat an acute condition (e.g., bleeding caused by surgery or trauma, or factor inhibitor/autoimmune episodes in subjects receiving coagulation replacement therapy) in single or multiple doses for a relatively short period, for example one to two weeks. In addition, fucoidan therapy may be used in combination with other hemostatic agents, blood factors, and medications. For example, the subject may be administered a therapeutically effective amount of one or more factors selected from the group consisting of factor XI, factor XII, prekallikrein, high molecular weight kininogen (HMWK), factor V, factor VII, factor VIII, factor IX, factor X, factor XIII, factor II, factor VIIa, and von Willebrands factor. Treatment may further comprise administering a procoagulant, such as an activator of the intrinsic coagulation pathway, including factor Xa, factor IXa, factor XIa, factor XIIa, and VIIIa, prekallekrein, and high-molecular weight kininogen; or an activator of the extrinsic coagulation pathway, including tissue factor, factor VIIa, factor Va, and factor Xa. In addition, transfusion of blood products may be necessary to replace blood loss in subjects experiencing excessive bleeding, and in cases of injury, surgical repair may be appropriate to stop bleeding.

The invention also provides a method for reversing the effects of an anticoagulant in a subject, the method comprising administering a therapeutically effective amount of a composition comprising purified fucoidan to the subject. In certain embodiments, the subject may have been treated with an anticoagulant including, but not limited to, heparin, a coumarin derivative, such as warfarin or dicumarol, TFPI, AT III, lupus anticoagulant, nematode anticoagulant peptide (NAPc2), active-site blocked factor VIIa (factor VIIai), factor IXa inhibitors, factor Xa inhibitors, including fondaparinux, idraparinux, DX-9065a, and razaxaban (DPC906), inhibitors of factors Va and VIIIa, including activated protein C (APC) and soluble thrombomodulin, thrombin inhibitors, including hirudin, bivalirudin, argatroban, and ximelagatran. In certain embodiments, the anticoagulant in the subject may be an antibody that binds a clotting factor, including but not limited to, an antibody that binds to Factor V, Factor VII, Factor VIII, Factor IX, Factor X, Factor XIII, Factor II, Factor XI, Factor XII, von Willebrands factor, prekallikrein, or high molecular weight kininogen (HMWK).

In certain embodiments, purified fucoidan extract can be administered alone or coadministered with one or more different fucoidans and/or in combination with one or more other therapeutic agents for reversing the effects of an anticoagulant in the subject. For example, the subject may be administered a therapeutically effective amount of a composition comprising a fucoidan and one or more factors selected from the group consisting of factor XI, factor XII, prekallikrein, high molecular weight kininogen (HMWK), factor V, factor VII, factor VIII, factor IX, factor X, factor XIII, factor II, factor VIIa, and von Willebrands factor. Treatment may further comprise administering a procoagulant, such as an activator of the intrinsic coagulation pathway, including factor Xa, factor IXa, factor XIa, factor XIIa, and VIIIa, prekallekrein, and high-molecular weight kininogen; or an activator of the extrinsic coagulation pathway, including tissue factor, factor VIIa, factor Va, and factor Xa.

In another aspect, the invention provides a method for improving clotting in a subject undergoing a surgical or invasive procedure, the method comprising administering a therapeutically effective amount of a composition comprising purified fucoidan to the subject. In certain embodiments, the fucoidan can be administered alone or coadministered with one or more different fucoidans and/or in combination with one or more other therapeutic agents to the subject undergoing a surgical or invasive procedure. For example, the subject may be administered a therapeutically effective amount of one or more factors selected from the group consisting of factor XI, factor XII, prekallikrein, high molecular weight kininogen (HMWK), factor V, factor VII, factor VIII, factor IX, factor X, factor XIII, factor II, factor VIIa, and von Willebrands factor. Treatment may further comprise administering a procoagulant, such as an activator of the intrinsic coagulation pathway, including factor Xa, factor IXa, factor XIa, factor XIIa, and VIIIa, prekallekrein, and high-molecular weight kininogen; or an activator of the extrinsic coagulation pathway, including tissue factor, factor VIIa, factor Va, and factor Xa.

In another aspect, the invention provides a method of inhibiting TFPI activity comprising combining a composition comprising TFPI with a sufficient amount of a fucoidan to inhibit TFPI activity. In certain embodiments, TFPI activity is inhibited in a subject by a method comprising administering a therapeutically effective amount of a composition comprising purified fucoidan extract to the subject. In certain embodiments, the invention provides a method of inhibiting TFPI activity in a biological sample, the method comprising combining the biological sample (e.g., blood or plasma) with a sufficient amount of purified fucoidan extract to inhibit TFPI activity.

3. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Purification of Fucoidan Trial 1

Day 1

Fucoidan extract (50 grams, NPNutra lot #050316-FU-85) was dissolved in 1,000 mL of high-purity water (NERL, lot #0808036) and stirred for 45 minutes at 40-45° C. in a water bath. The solution was at a pH of 5.82 and a temperature of 41° C. when 2.5 grams of disodium EDTA was added with stirring (2.5% wEDTA/w starting Fucoidan extract, EDTA lot #006139 from Fisher). The solution pH dropped to 4.70 as the EDTA dissolved, but was then adjusted upwards to 6.02 with 0.1 M NaOH. The reaction was then mixed and maintained for 1 hour at 40-45° C. and pH 6.0 (±0.2). After 1 hour, 24 grams of sodium chloride (2% w/v, Fisher Lot #010166) was added and the water jacket was removed. The pH was then adjusted from pH 5.7 to 5.95 w/0.1 M NaOH. The fucoidan was precipitated by admixing approximately one volume of absolute ethanol (1.1 liter, Sigma-Aldrich Lot #06563JE), and allowing precipitation to occur overnight at ambient temperature.

Day 2

The supernatant solution was removed by aspiration from the polysaccharide precipitate. The precipitate was then re-dissolved by addition of 1 liter (1,000 mL) of room-temperature, high purity water, followed by 30-60 minutes of vigorous stirring. Once the precipitate was in solution, 20 grams (2% w/v) of sodium chloride was dissolved by continued mixing of the solution. The polysaccharide was again precipitated by admixing 800 mL of absolute ethanol with the resolubilized, resalinized precipitate from Day 1. Again, the polysaccharide was allowed to precipitate overnight.

Day 3

The supernatant solution was again removed from the Day 2 precipitate, and the entire process of resolubilization (1,000 mL NERL water), resalinization (20 grams of NaCl), and reprecipitation (800 mL of absolute ETOH) was repeated on Day 3. The fucoidan was again allowed to precipitate overnight.

Day 4

On Day 4, the supernatant was removed by aspiration from the polysaccharide precipitate. The precipitate was then dissolved by mixing with 900 mL of high-purity water for 1-1.5 hours at 22° C. The pH, which measured at 6.85, was adjusted to pH 5.8 by addition of 6 N HCl. The entire solution was then filtered through a 0.2 µm KLEENPAK N66 POSIDYNE filter capsule (Pall, Lot #IJ7287). The flask and filter were then rinsed with about 100 mL of high-purity water, which was then filtered though the POSIDYNE filter and added to the polysaccharide solution. The entire filtered solution (~1.05 liters) was then loaded into a single freeze-dryer tray and frozen at −40° C. for 3 hours. Freeze-drying was then conducted over the next approximately 48 hours with the following program: First 4 hours, shelf temperature at 10° C., next 20 hours, shelf temperature at 20° C., final 24 hours, shelf temperature at 50° C. The dried product was then removed from the dryer and tray and placed into a pre-tared plastic container.

The product yield was 26.4 grams (52.8% weight yield). The product was labeled as Lot/trial 1 and placed into double poly bags for storage.

Example 2

Purification of Fucoidan Trial 2

Day 1

Fucoidan extract (50 grams, NPNutra lot #050316-FU-85) was dissolved in 1,000 mL of high-purity water (NERL, lot #0808036) by stirring for 30-45 minutes at 40-45° C. in a water bath. The solution was at a pH of 5.83 and a temperature of 42.5° C. when 1.25 grams of disodium EDTA was added with stirring (1.25% wEDTA/w fucoidan extract, EDTA lot #006139 from Fisher). The solution pH dropped to 4.90 as the EDTA dissolved, but was then adjusted upwards to 6.04 with 0.1 M NaOH. The reaction was then mixed and maintained for 1 hour at 40-45° C. and pH 6.0 (±0.2). The solution pH was 6.15 at the end of the 1 hour incubation, as 22 grams of sodium chloride was admixed into the solution. The pH dropped slightly to 55.72 but was then adjusted to 6.08 with 1 M NaOH. Fucoidan was precipitated by addition of 1 liter (1,000 mL) of absolute ETOH. The precipitate was allowed to settle at room temperature overnight.

Day 2

The supernatant solution was removed by aspiration from the polysaccharide precipitate. The precipitate was then re-dissolved by addition of 1 liter (1,000 mL) of room-temperature, high purity water, followed by 30-60 minutes of vigorous stirring. Once the precipitate was in solution, 20 grams (2% w/v) of sodium chloride was dissolved by continued mixing of the solution. The polysaccharide was again precipitated by admixing 750 mL of absolute ethanol with the resolubilized, resalinized precipitate from Day 1. Again, the polysaccharide was allowed to precipitate overnight.

Day 3

The supernatant solution was again removed from the Day 2 precipitate, and the entire process of resolubilization (1,000 mL NERL water), resalinization (20 grams of NaCl), and reprecipitation (750 mL of absolute ETOH) was repeated on Day 3. The fucoidan was again allowed to precipitate overnight.

Day 4

On Day 4, the supernatant was removed by aspiration from the polysaccharide precipitate. The precipitate was then dissolved by mixing with 900 mL of high-purity water for 1-2 hours at 22° C. The pH, which measured at 6.81, was then adjusted to pH 5.82 by addition of 6 N HCl. The entire solution was then filtered through a 0.2 μm KLEENPAK N66 POSIDYNE filter capsule (Pall, Lot #U7287). The flask and filter were then rinsed with about 100 mL of high-purity water, which was then filtered though the POSIDYNE filter and added to the polysaccharide solution. The entire filtered solution (~1.1 liters) was then loaded into a single freeze-dryer tray and frozen at −40° C. for 3 hours. Freeze-drying was then conducted over the next approximately 48 hours with the following program: First 4 hours, shelf temperature at 10° C., next 20 hours, shelf temperature at 20° C., final 24 hours, shelf temperature at 50° C. The dried product was then removed from the dryer and tray and placed into a pre-tared plastic container.

The product yield was 25.4 grams (50.8% weight yield). The product was labeled as Lot/trial 2 and placed into double poly bags for storage.

Example 3

Analysis of Fucoidan Samples

Samples of purified fucoidan extracts from Trial 1 (Example 1) and Trial 2 (Example 2) were characterized and compared to crude fucoidan extract (NPNutra lot #050316-FU-85). Sample analyses were performed by the Bay Bioanalytical Laboratory, Inc. (BBL, Hercules, Calif.). Characterization of fucoidan extracts included size exclusion chromatography with laser light scattering (LLS) detection, fucose and xylose content, water content, heavy metals, sulfate, and elemental analysis. Size exclusion chromatography with LLS was used to measure average molecular weight. Fucose and xylose were determined by hydrolyzing the fucoidan and measuring fucose and xylose content by HPLC using a column designed to separate small carbohydrates. The total carbohydrate content was also estimated by using a phenol-sulfuric acid assay with fucose as the standard. The water content was measured by using a Karl Fischer (KF) assay. Sulfate was measured by ion exchange chromatography, and cations (principally sodium, potassium, and other heavy metals) were measured by ICP-MS. In addition, elemental composition analysis (CHNS) was performed on samples. The Complex Carbohydrate Research Center (University of Georgia, Athens, Ga.) performed monosaccharide analysis via GC/MS following preparation of per-O-trimethylsilylated methyl glycosides from the sample. Endotoxin by LAL was determined at Avigen. The results are summarized in Table 1.

TABLE 1

Summary of Fucoidan Extract Characterization Results

| | NP Nutra 050316-FU-85 (MC514) | Processed Trial #1 (AN50) | Processed Trial #2 (AN51) |
|---|---|---|---|
| $M_w$ | 184,800 | 179,400 | 183,800 |
| % w/w Neutral Sugars by phenol-$H_2SO_4$ | 52 | 73 | 65 |
| Monosaccharide (%) | | | |
| Fucose | 60.7 | 60.3 | 61.1 |
| Xylose | 22.8 | 27.4 | 24.9 |
| Glucose | 5.5 | 1.6 | 0.8 |
| Galactose | 3.9 | 0.6 | ND |
| Mannose | 3.3 | ND | 4.0 |
| Galacturonic Acid | 2.4 | 2.2 | 3.1 |
| Glucaronic Acid | 1.4 | ND | ND |
| Rhaminose | ND | 4.3 | 6.1 |
| % Sulfate | 11.6 | 16.9 | 15.5 |
| % water by KF | 8.4 | 9.2 | 9.0 |
| Elemental Analysis: % w/w | | | |
| Carbon | 30.4 | 27.7 | 25.5 |
| Hydrogen | 4.7 | 4.0 | 3.2 |
| Nitrogen | 0.7 | 0.2 | 0.3 |
| Sulfur | 6.6 | 6.2 | 6.0 |
| Cation (top 8): ppm | | | |
| Sodium | 50000 | 75000 | 80000 |
| Magnesium | 8200 | 1200 | 1200 |
| Calcium | 6300 | 5400 | 6900 |
| Potassium | 4900 | 550 | 530 |
| Iron | 370 | 60 | 102 |
| Strontium | 310 | 460 | 480 |

TABLE 1-continued

Summary of Fucoidan Extract Characterization Results

|  | NP Nutra 050316-FU-85 (MC514) | Processed Trial #1 (AN50) | Processed Trial #2 (AN51) |
|---|---|---|---|
| Phosphorous | 160 | 27 | 30 |
| Aluminum | 43 | 27 | 40 |
| Endotoxin (EU/mg) | 88.6 | 38 | 40 |

The sample analyses are described in further detail below.

A. Laser Light Scattering (LLS)

The fucoidan extracts were analyzed for molecular weight using size exclusion HPLC with detection by laser light scattering (LLS) and refractive index (RI), as described in BBL publication SOP-059, herein incorporated by reference. Each sample was dissolved in the mobile phase at a final concentration of approximately 10 mg/mL. Dextran obtained from American Polymer Standards was used as a system control. The following instrumentation and parameters were used:

Instrumentation and Setup

Mobile Phase: 0.1 M Ammonium Acetate
Column: Shodex OH pack SB-803 HQ 30 cm×8 mm (with guard column)
Pump: ASI Model 500
Injector: Varian 9010 autosampler equipped with 100 μL loop
LLS Detector: Precision Detectors PD2020 Multi-Detector Light Scattering System (90° Classical)
RI Detector: Shodex RI SE-61
Injection Vol: 100 μL
Flow Rate: 1 mL/min
Analysis Time: 20 min
Data System: Precision Discovery 32 v. 0.98.010

Instrument calibration was performed using NIST BSA lot 927c with a differential index of refraction (dn/dc) value of 0.185 mL/g. Calculations for the dextran control molecular weight were based on a dn/dc of 0.147 mL/g, as reported by American Polymer Standards. Calculations for molecular weight of the samples used a dn/dc of 0.137 mL/g, which was obtained from Sigma technical support. Single injections were made for each sample.

The results of molecular weight (MW) measurements of the fucoidan samples are summarized in Table 2.

TABLE 2

Weight Average Molecular Weight ($M_w$) by LLS

|  | NP Nutra 050316-FU-85 (MC514) | Processed Trial #1 (AN50) | Processed Trial #2 (AN51) |
|---|---|---|---|
| $M_w$ | 184,800 | 179,400 | 183,800 |
| % <10 kDa | 4.7 | <1 | <1 |
| % 10-50 kDa | 22.3 | 18.7 | 19.4 |
| % 50-100 kDa | 13.0 | 13.0 | 11.3 |
| % >100 kDa | 60.0 | 68.3 | 69.3 |

The results show a significant difference in molecular weight among the three crude samples. In general molecular weight values can vary by approximately 10% within a laboratory.

B. Hydrolysis of Fucoidan and Measurement of Fucose and Xylose by HPLC

The samples were dissolved in 2M HCl to yield approximately 10 mg/mL solutions. Five 1 mL aliquots of each sample were incubated at 60° C. in 4 mL glass vials for different periods of time. One vial of each sample was removed after 2, 4, 6, 8, and 10 hours and neutralized by the addition of 1 mL of chilled 2M NaOH.

The samples were analyzed for fucose and xylose content by HPLC with refractive index detection. L-Fucose (Sigma-Aldrich, lot #105K1058) and D-Xylose (Fluka lot #1118093) in water were used as the standards for the quantitation. The following instrumentation and parameters were used:

Instrumentation and Setup

Mobile Phase: 5 mM Sulfuric Acid
Column: Bio-Rad Aminex HPX-78H, 300 mm×7.8 mm (with guard column)
Pump: ASI Model 500
Injector: Varian 9010 autosampler equipped with 20 μL loop
RI Detector: Shodex RI SE-61
Injection Vol: 20 μL
Flow Rate: 0.8 mL/min
Analysis Time: 18 min
Column Temperature: ambient The fucose and xylose contents in the three fucoidan extracts were determined by HPLC following hydrolysis in 2N HCl at 60° C. for 22 hours. The results are summarized in Table 3A. The % w/w values in the tables have been corrected for gain of water during hydrolysis: ((164-18)/164) fucose % w/w or ((150-18)/150) xylose % w/w.

TABLE 3A

Fucose and xylose content (60° C., 22 hours)

|  | NP Nutra 050316-FU-85 (MC514) | Processed Trial #1 (AN50) | Processed Trial #2 (AN51) |
|---|---|---|---|
| % w/w Fucose | 11.1 | 8.6 | 8.7 |
| % w/w Xylose | 5.8 | 4.9 | 4.9 |

These values are considerably lower than expected, indicating that hydrolysis was probably not complete. Two of the samples were hydrolyzed with the sample concentration at 1 mg/mL in 2N HCl at 100° C. for 8 hours. The results are summarized in Table 3B.

TABLE 3B

Fucose and xylose content (100° C., 22 hours)

|  | NP Nutra 050316-FU-85 (MC514) | Processed Trial #1 (AN50) |
|---|---|---|
| % w/w Fucose | 21.7 | 19.2 |
| % w/w Xylose | 5.3 | 5.5 |

The samples were also analyzed for total neutral sugars by the phenol-sulfuric acid assay, a classic colorimetric assay. Fucose was used as the standard.

These results were not corrected for the gain of water during hydrolysis, so are high by a few percent, but close to the expected values. The results are summarized in Table 3C.

TABLE 3C

Phenol-Sulfuric Acid Assay of Fucose Content

| | NP Nutra 050316-FU-85 (MC514) | Processed Trial #1 (AN50) | Processed Trial #2 (AN51) |
|---|---|---|---|
| Neutral sugars % w/w (Fucose standard) | 46 | 65 | 58 |

C. Water Content

The water content of each fucoidan extracts was determined by Karl Fischer (KF) assay, according to BBL publication SOP-009 v6 "Karl Fischer Moisture Content Assay of Bulk Drug Using Anhydrous Methanol Extraction," herein incorporated by reference. For Karl Fischer assays, approximately 15 mg of each sample was weighed into a clean 1.8 mL autosampler vial. Samples were prepared in triplicate. Water was extracted from the samples by injecting approximately 1 mL of methanol into the closed sample vials. The results are summarized in Table 4.

TABLE 4

Water Content

| | NP Nutra 050316-FU-85 (MC514) | Processed Lot #1 (AN50) | Processed Lot #2 (AN51) |
|---|---|---|---|
| assay 1 | 8.6 | 9.2 | 9.1 |
| assay 2 | 8.1 | 9.1 | 9.0 |
| assay 3 | — | 9.2 | 8.8 |
| average | 8.4 | 9.2 | 9.0 |

Units are % w/w ((weight of water/total sample weight)100).

D. Metals, Elemental Analysis, and Sulfate Analysis

A heavy metals screen was performed using ICP-MS by West Coast Analytical Services, Inc. Sulfur was determined quantitatively by ICP-MS. Analysis for carbon, hydrogen, nitrogen, and sulfur (CHINS) content was also performed by West Coast Analytical Services using an elemental analyzer. Sulfate was also determined by ion chromatography at West Coast Analytical Services on fucoidan samples hydrolyzed in 6N HCl for 6 hours.

The results of sulfate determination by ion chromatography are shown in Table 5. The % w/w values in the tables have been corrected for gain of water during hydrolysis: ((96-16)/96) sulfate % w/w.

TABLE 5

Sulfate Content

| | NP Nutra 050316-FU-85 (MC514) | Processed Lot #1 (AN50) | Processed Lot #2 (AN51) |
|---|---|---|---|
| % w/w Sulfate | 11.6 | 16.9 | 15.5 |

Results of the screen of elements by ICP-MS are shown in Tables 6A and 6B. Values are reported in μg/g (ppm).

TABLE 6A

Most Abundant Elements

| Metal | NP Nutra 050316-FU-85 (MC514) | Processed Lot #1 (AN50) | Processed Lot #2 (AN51) |
|---|---|---|---|
| Sodium | 50000 | 75000 | 80000 |
| Magnesium | 8200 | 1200 | 1200 |
| Potassium | 4900 | 550 | 530 |
| Calcium | 6300 | 5400 | 6900 |
| Iron | 370 | 60 | 102 |
| Strontium | 310 | 460 | 480 |
| Phosphorus | 160 | 27 | 30 |
| Aluminum | 43 | 27 | 40 |
| Manganese | 35 | 0.19 | 0.14 |
| Barium | 33 | 52 | 52 |
| Titanium | 15 | 11 | 15 |

TABLE 6B

Trace Contaminants

| Metal | NP Nutra 050316-FU-85 (MC514) | Processed Lot #1 (AN50) | Processed Lot #2 (AN51) |
|---|---|---|---|
| Arsenic | 2.1 | ND | ND |
| Bromine | 9.5 | ND | ND |
| Cerium | 0.08 | ND | ND |
| Chromium | 12 | 7.2 | 8.2 |
| Cobalt | 0.49 | ND | ND |
| Iodine | 14 | 1.6 | 1.5 |
| Lead | 0.18 | ND | ND |
| Lithium | 0.64 | ND | ND |
| Manganese | 35 | 0.19 | 0.14 |
| Molybdenum | 0.15 | ND | ND |
| Nickel | 3.8 | 0.65 | 0.63 |
| Rubidium | 2.2 | 0.33 | 0.29 |
| Tin | 0.27 | ND | ND |
| Tungsten | 0.11 | ND | ND |
| Uranium | 0.55 | 0.34 | 0.36 |
| Vanadium | 0.89 | ND | ND |

The results of the elemental composition analysis are shown in Tables 7A and 7B. The elemental composition analysis can be compared with the theoretical composition, calculated for a fucoidan residue containing only fucose and one sulfate per fucose as weight percent, e.g. $C_6H_{12}O_5+SO_3-H_2O=C_6H_{10}O_7S$ (fucose residue+1 sulfate), see Table 7B. The elemental composition determined for all lots agree well with the expected theoretical value with the exception of sulfur. Thus, it is unlikely that each fucose residue is sulfated. The sulfur values correlate well with the sulfate ion analysis. The nitrogen values are low probably due to other non-fucoidan material extracted with the fucoidan.

TABLE 7A

Elemental Analysis (% w/w)

| | NP Nutra 050316-FU-85 (MC514) | Processed Lot #1 (AN50) | Processed Lot #2 (AN51) | Theory |
|---|---|---|---|---|
| Carbon | 30.4 | 27.7 | 25.5 | 31.9 |
| Hydrogen | 4.7 | 4.0 | 3.2 | 4.4 |
| Nitrogen | 0.7 | 0.2 | 0.3 | 0 |
| Sulfur | 6.6 | 6.2 | 6.0 | 14.2 |

TABLE 7B

Mass Balance of Fucoidan

|  | NP Nutra 050316-FU-85 (MC514) | Processed Trial #1 (AN50) | Processed Trial #2 (AN51) |
| --- | --- | --- | --- |
| Neutral sugars (by phenol/H$_2$SO$_4$, corrected as residue) | 46 | 65 | 58 |
| Water (by KF) | 8.4 | 9.2 | 9.0 |
| Sulfate(corrected as residue) | 11.6 | 16.9 | 15.5 |
| Cations (Na + K + Mg + Ca) | 5.5 | 8.2 | 8.9 |
| Total | 71.5 | 99.3 | 91.4 |

E. Monosaccharide Composition

Monosaccharide Composition was determined by GC/MS at the Complex Carbohydrate Research Center (University of Georgia, Athens, Ga.). Methyl glycosides were prepared from 10 ug of sample by treating with 1M HCl in methanol (25 drops) at 80° C. for 15 h followed by re-N-acetylation with pyridine (5 drops) and acetic anhydride (5 drops) in methanol (20 drops) at room temperature for 1 hour. The samples were then per-O-trimethylsilylated by the treatment with Tri-Sil (10 drops, Pierce) at 80° C. (15 minutes). These procedures were carried out as previously described by Merkle and Poppe in Methods Enzymol. 1994, 230, 1-15 and York et al. in Methods Enzymol 1985, 118, 3-40. GC/MS analysis of the TMS methyl glycosides was performed on an HP 5890 GC interfaced to a 5970 MSD, using DB-1 column (30 m ×0.25 mm ID). The results are shown in Table 8.

TABLE 8

Monosaccharide Analysis

|  | Parent Lot (NP-051316) | Trial Lot #1 | Trial Lot #2 |
| --- | --- | --- | --- |
| Fucose | 60.7 | 60.3 | 61.1 |
| Xylose | 22.8 | 27.4 | 24.9 |
| Glucose | 5.5 | 1.6 | 0.8 |
| Galactose | 3.9 | 0.6 | ND |
| Mannose | 3.3 | ND | 4.0 |
| Galacturonic Acid | 2.4 | 2.2 | 3.1 |
| Glucaronic Acid | 1.4 | ND | ND |
| Rhaminose | ND | 4.3 | 6.1 |

The monosaccharide composition was not greatly impacted by processing, despite the 50% loss of mass over the processing and the increase in total neutral sugars and sulfate.

F. Endotoxin

Bacterial endotoxin was determined by LAL according to USP<85>. The results are shown in Table 9 below. Processing resulted in an approximate 50% reduction in endotoxin levels.

TABLE 9

Endotoxin levels of unprocessed and processed Fucoidan.

|  | Endotoxin (EU/mg) |
| --- | --- |
| Parent Lot (NP-051316) | 88.6 |
| Trial Lot #1 | 38 |
| Trial Lot #2 | 40 |

Example 4

Biological Activity of Fucoidan Samples

Samples of purified fucoidan extracts from Trial 1 (Example 1) and Trial 2 (Example 2) were evaluated in in vitro clotting assays for activity and compared to crude fucoidan extract (NPNutra lot #050316-FU-85). Purified and crude fucoidan extracts were evaluated for biological activity in in vitro assays eg., APTT, dPT and thromboelastograph at Avigen Inc.

Plasma Clotting Assays:

Activated Partial Thromboplastin Time (APTT)

The APTT assay was modified from standard procedures (Anderson 1976; Staff 2004). Briefly, 5 µL of 20× fucoidan in saline was incubated with 95 µL plasma for 30 min at room temperature. Then, 100 µL of 37° C. APTT reagent was added to the mixture and incubated at 37° C. for 3 min followed by addition of 100 µL of 37° C. 25 mM CaCl$_2$ and initiation of timing in a standard fibrometer.

Dilute Prothrombin Time (dPT)

The dPT assay was similar to that previously described (14). Simplastin (bioMeriex, Durham, N.C.) was diluted with saline to 1:100 or 1:300, depending on the assay format, and mixed with 25 mM CaCl$_2$. The plasma sample was also pre-warmed to 37° C. and then ~75 µL of each were mixed together and time to clot was measured with a fibrometer. For evaluation of fucoidan activity, 5 µL of 20× fucoidan was pre-incubated with plasma at room temperature for 30 min before initiating the dPT assay. To assess potential inhibition of TFPI activity by fucoidan, diluted rTFPI (American Diagnostica, Stamford, Conn.) was preincubated with fucoidan for 5 min at room temperature, plasma sample was added, and the mixture was incubated for an additional 25 min followed by dPT initiation. All clotting studies were performed in duplicate and reproduced.

Plasma Thromboelastograph (TEG)

Sample preparation—Factor VIII deficient human plasma (George King Biomedical, Overland Park, Kans.) samples (360 µL) pre-warmed to 37° C. was mixed with 40 µL of unprocessed or EDTA-treated fucoidan in saline solution. The final fucoidan concentration in the plasma samples ranged from 1 µg/mL to 100 µg/mL.

TEG analysis—For activation of the plasma samples, 20 µL of 0.2 M CaCl$_2$ were added into a plastic cup mounted on an aluminum cup holder. The mixtures of plasma sample and fucoidan (340 µL) were dispensed into the CaCl$_2$ solution and immediately measured. The TEG analyzer incubated the samples continuously at 37° C. The tests were stopped after the following clot formation parameters were calculated by the TEG® Analytical Software Version 4: R, latency period for initial coagulation from the time the measurement started; angle α, representing the rapidity of clot strengthening; and MA (maximum amplitude), equivalent to the maximum strength of the formed clot. In plasma samples without clot formation the measurement was ended after 2 h. The average values and standard deviations were calculated from three independent measurements.

Figure 1:
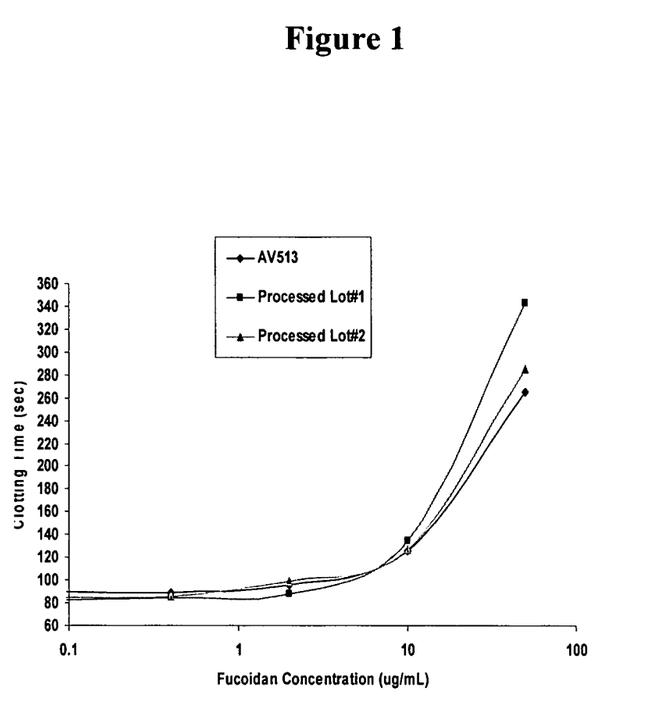
FIG. 1 shows the effect of processing on the activity of fucoidan (AV513) in an activated partial thromboplastin time (APTT) assay.
Figure 2:
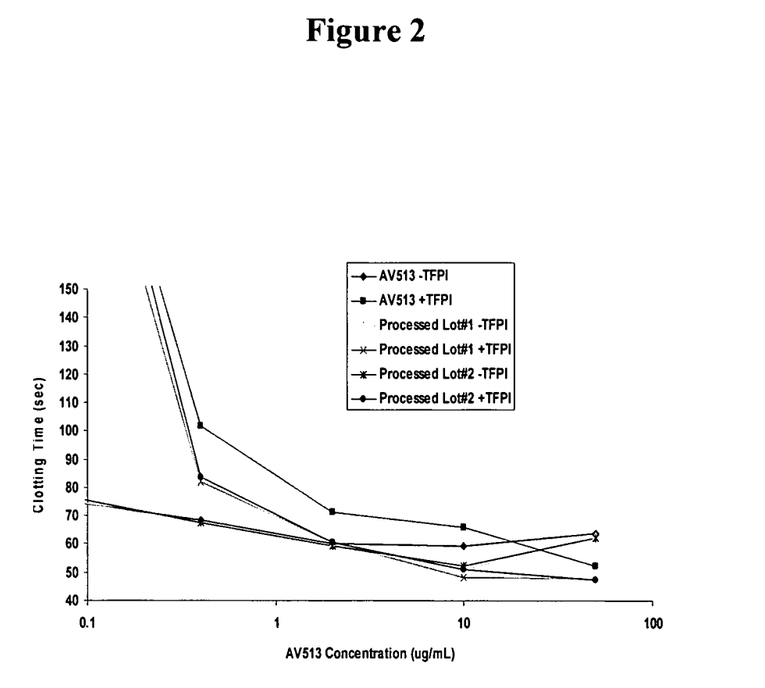
FIG. 2 shows the effect of processing on the activity of fucoidan in a dilute prothrombin time (dPT) assay.

The effect of processing on the activity of Fucoidan on the intrinisic and extrinsic clotting pathway was examined by measuring the clotting time vs. Fucoidan concentration in the APPT (FIG. 1) and dPT (FIG. 2) assays. As can be seen in FIG. 1 processing had a modest change in APTT activity. However, as seen in FIG. 2, Fucoidan enhances TFPI inhibition by decreasing clotting time and shifts the dose response (IC90's for crude fucoidan extract is approx. 30 µg/mL vrs purified fucoidan extract lots #1 and #2 are aprrox. 4 µg/mL.

Figure 3:
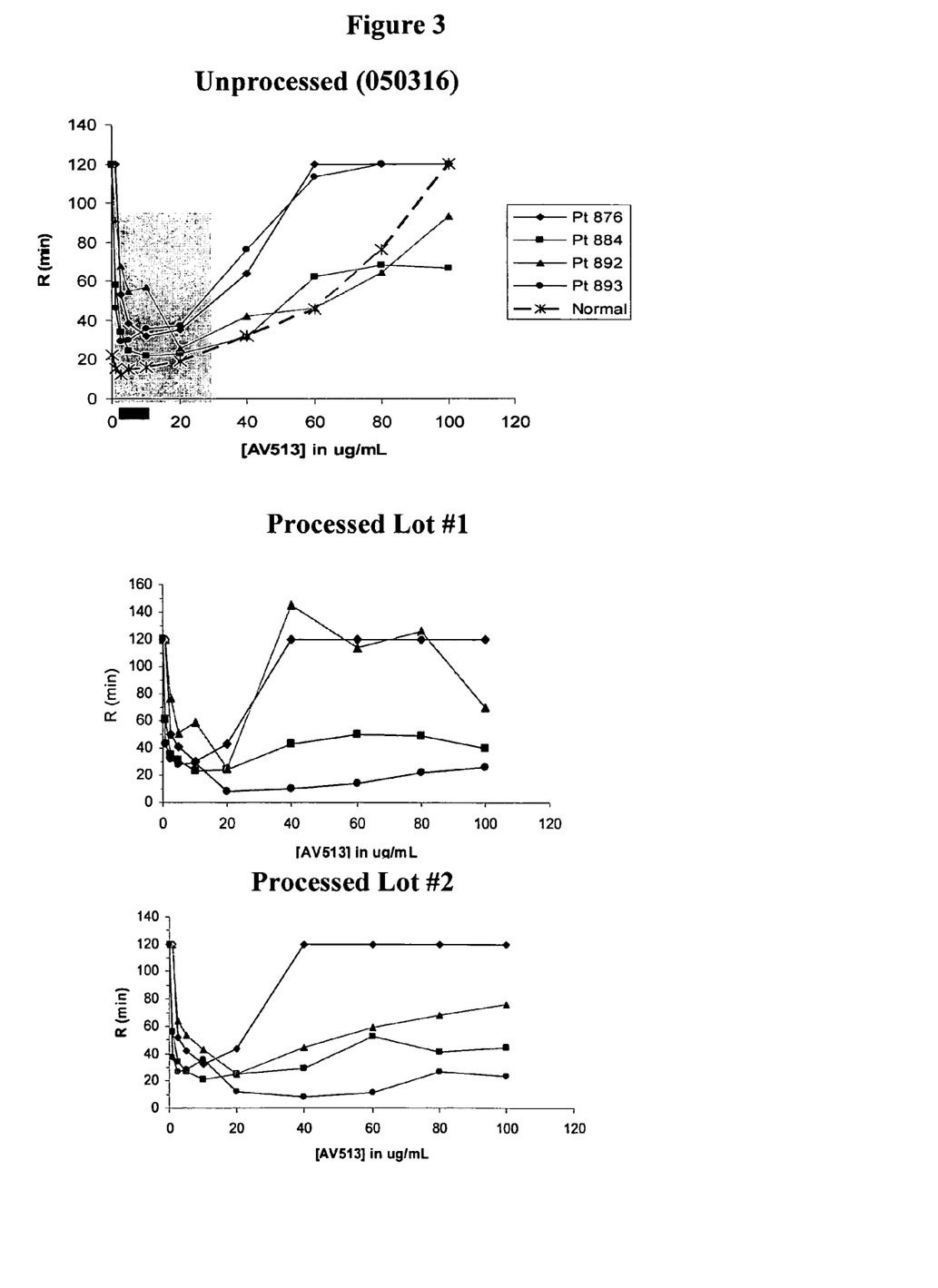
FIG. 3 shows a thromboelastograph (TEG) analysis of the effect of processing on the activity of fucoidan.

The impact of processing on the pro- and anti-coagulation activities in human HemA plasma as measured by TEG analysis was examined in plasma samples from four separate Hemophilia A patients. The R value is plotted against concentration where the R values represents the time it takes to form a clot of 20 mm size. As depicted in FIG. 3, while crude fucoidan extract and purified fucoidan extracts demonstrated similar pro-coagulant profile in all four Hem A plasma's, the effect on anti-coagulation varied. Processed lots #1 and #2 containing fucoidan showed altered anti-coagulant activity in some samples.

E. Conclusion

Purified fucoidan extract as described in Examples 1 and 2 had increased neutral sugar and sulfate content and reduced heavy metal contamination and endotoxin levels, while maintaining the monosaccharide profile. The purified fucoidan extracts had non-detectable (ND) levels of arsenic, bromine, cerium, cobalt, lead, lithium, molybdenum, tin, tungsten, and vanadium. In addition, purification reduced levels of iodine, iron, magnesium, manganese, nickel, phosphorus, potassium, and rubidium by at least two-fold. Endotoxin levels were reduced approximately 50%. Purified fucoidan extracts containing enriched fucoidan had accelerated clotting activity (and enhanced TFPI inhibition) and minimal change in anti-coagulant activity when compared to the crude fucoidan extract.

While the preferred embodiments of the invention have been illustrated and described, it will be appreciated that various changes can be made therein without departing from the spirit and scope of the invention.

What is claimed is:

1. A method for purifying fucoidan from a heterogeneous mixture, the method comprising:
    (a) providing a source of fucoidan;
    (b) removing heavy metal ions from said source by treating with a chelating agent immobilized on a solid support to produce a first fucoidan mixture;
    (c) selectively precipitating fucoidan present in said first fucoidan mixture to remove contaminants;
    (d) resuspending fucoidan-containing precipitate in aqueous solution to produce a second fucoidan mixture;
    (e) repeating steps (c) and (d) one or more times; and
    (f) filtering the aqueous solution comprising fucoidan to remove bacterial and endotoxin contaminants to yield purified fucoidan.

2. The method of claim 1, wherein the fucoidan possesses from 5 to 25 percent by weight sulfur.

3. The method of claim 2, wherein the fucoidan is of algal origin.

4. The method of claim 3, wherein the fucoidan is from the genus *Fucus* or *Laminari*.

5. The method of claim 4, wherein the fucoidan is from *Fucus vesiculosis* or *Laminaria japonica*.

6. The method of claim 1, wherein the chelating agent is selected from the group consisting of ethylene diamine tetra acetic acid (EDTA), ethyleneglycol-bis-(beta-aminoethyl ether)N,N,N',N'-tetraacetic acid (EGTA), 2,3-dimercapto-propanel-1-sulfonic acid (DMPS), and 2,3-dimercaptosuccinic acid (DMSA).

7. The method of claim 6, wherein the chelating agent is EDTA.

8. The method of claim 1, wherein the chelating agent immobilized on the solid support is an iminodiacetate chelating resin.

9. The method of claim 1, wherein the fucoidan in said first fucoidan mixture is selectively precipitated with ethanol.

10. The method of claim 9, wherein the concentration of ethanol is about 40% to 50% (v/v).

11. The method of claim 9, wherein the pH is maintained between about pH 5.7 to about pH 6.0.

12. The method of claim 11, wherein the pH is adjusted to about pH 5.95.

13. The method of claim 9, wherein NaCl is added to the fucoidan mixture at a concentration of about 20-24 g/liter.

14. The method of claim 1, comprising repeating steps (c) and (d) three times.

15. The method of claim 1, further comprising lyophilization of the purified fucoidan.

16. A composition comprising purified fucoidan produced by the method of claim 1, wherein said composition has non-detectable levels of arsenic, bromine, cerium, cobalt, lead, lithium, molybdenum, tin, tungsten and vanadium.

17. The composition of claim 16, wherein the fucoidan is biologically active.

18. The composition of claim 17, wherein the fucoidan has pro-coagulant activity.

19. The composition of claim 16, further comprising a pharmaceutically acceptable excipient.

20. A method for treating a subject in need of enhanced blood coagulation comprising administering a therapeutically effective amount of the composition of claim 16 to said subject.

21. The method of claim 20, wherein the fucoidan is administered at a dosage of about 0.01 mg/kg to about 100 mg/kg.

22. The method of claim 20, wherein the subject has a bleeding disorder selected from the group consisting of a chronic or acute bleeding disorder, a congenital coagulation disorder caused by a blood factor deficiency, and an acquired coagulation disorder.

23. The method of claim 20, wherein the subject is in need of improved hemostasis in an acute injury or wound setting.

24. The method of claim 20, wherein the cause of the need for enhanced blood coagulation is prior administration of an anticoagulant, surgery, or other invasive procedure.

25. The method of claim 20, wherein the cause of the need is as an anti-inflammatory agent, anti-cancer agent, anti-viral agent, or for mobilizing hematopoietic progenitor cells.

* * * * *